(12) United States Patent
Nguyen et al.

(10) Patent No.: US 7,981,054 B2
(45) Date of Patent: Jul. 19, 2011

(54) ALL-IN-ONE BIOLOGICAL SPECIMEN COLLECTING, TRANSPORTING AND ANALYZING DEVICE

(75) Inventors: Phuong Nguyen, San Diego, CA (US); Henri J. A. Charmasson, San Diego, CA (US)

(73) Assignee: Phuong Nguyen, San Diego, CA (US)

( * ) Notice: Subject to any disclaimer, the term of this patent is extended or adjusted under 35 U.S.C. 154(b) by 660 days.

(21) Appl. No.: 11/879,233

(22) Filed: Jul. 16, 2007

(65) Prior Publication Data
US 2009/0024055 A1 Jan. 22, 2009

(51) Int. Cl.
*A61B 5/00* (2006.01)
*A61B 10/00* (2006.01)
*B65D 81/00* (2006.01)

(52) U.S. Cl. ........ 600/577; 600/562; 600/573; 600/575; 600/576; 600/579

(58) Field of Classification Search .......... 600/562–584; 604/6.15, 317–326, 403–416
See application file for complete search history.

(56) References Cited

U.S. PATENT DOCUMENTS

| | | | |
|---|---|---|---|
| 4,116,066 A * | 9/1978 | Mehl et al. ................. | 73/864.52 |
| 4,184,483 A | 1/1980 | Greenspan | |
| 4,300,404 A * | 11/1981 | Mehl et al. ................. | 73/863.52 |
| 4,735,905 A | 4/1988 | Parker | |
| 4,842,826 A | 6/1989 | Guala | |
| 5,108,386 A | 4/1992 | Finneran | |
| 5,143,627 A | 9/1992 | Lapidus et al. | |
| 5,230,865 A | 7/1993 | Hargett et al. | |
| 5,422,273 A | 6/1995 | Garrison et al. | |
| 5,429,803 A | 7/1995 | Guirguis | |
| 5,431,884 A | 7/1995 | McDonough et al. | |
| 5,595,187 A * | 1/1997 | Davis ........................... | 600/584 |

(Continued)

FOREIGN PATENT DOCUMENTS

EP 1014088 12/1999
(Continued)

OTHER PUBLICATIONS

PCT International Search Report for corresponding Application No. PCT/US2008/007075.

*Primary Examiner* — Jeffrey G Hoekstra
(74) *Attorney, Agent, or Firm* — Charmasson Buchaca & Leach, LLP

(57) ABSTRACT

A device for collecting, shipping and analyzing a pathological specimen comprises a collector stick projecting from the inside of the stopper of a first tubular vessel containing a solution. The bottom of the vessel has a hole sealed by a frangible barrier. When the first vessel is inserted into a second vessel containing a signaling element and having a pintle projecting inwardly from its bottom, the frangible barrier is broken by the pintle and part of the solution flows into the second vessel where it contacts the signaling element. A pin projecting from the inside of a cover for the second vessel punctures the stopper of the first vessel facilitating the flow of solution from the first to the second vessel. The analytical process can be performed in the absence of any contacting or manipulating of the first vessel and specimen collector by simply screwing the cap to its farthest position.

10 Claims, 1 Drawing Sheet

U.S. PATENT DOCUMENTS

| | | | |
|---|---|---|---|
| 5,624,554 A | 4/1997 | Faulkner et al. | |
| 5,674,456 A | 10/1997 | Chess et al. | |
| 5,833,928 A | 11/1998 | Ratajczak et al. | |
| 6,277,646 B1 * | 8/2001 | Guirguis et al. | 436/165 |
| 6,358,474 B1 | 3/2002 | Dobler et al. | |
| 6,846,028 B2 | 1/2005 | Pratt | |
| 7,195,602 B2 * | 3/2007 | Yong et al. | 600/573 |
| 7,282,181 B2 | 10/2007 | Hudak et al. | |
| 7,517,495 B2 * | 4/2009 | Wu et al. | 422/61 |
| 2006/0139631 A1 * | 6/2006 | Feldsine et al. | 356/244 |
| 2006/0188939 A1 | 8/2006 | Gao | |

FOREIGN PATENT DOCUMENTS

| | | |
|---|---|---|
| WO | 9902958 | 1/1999 |

* cited by examiner

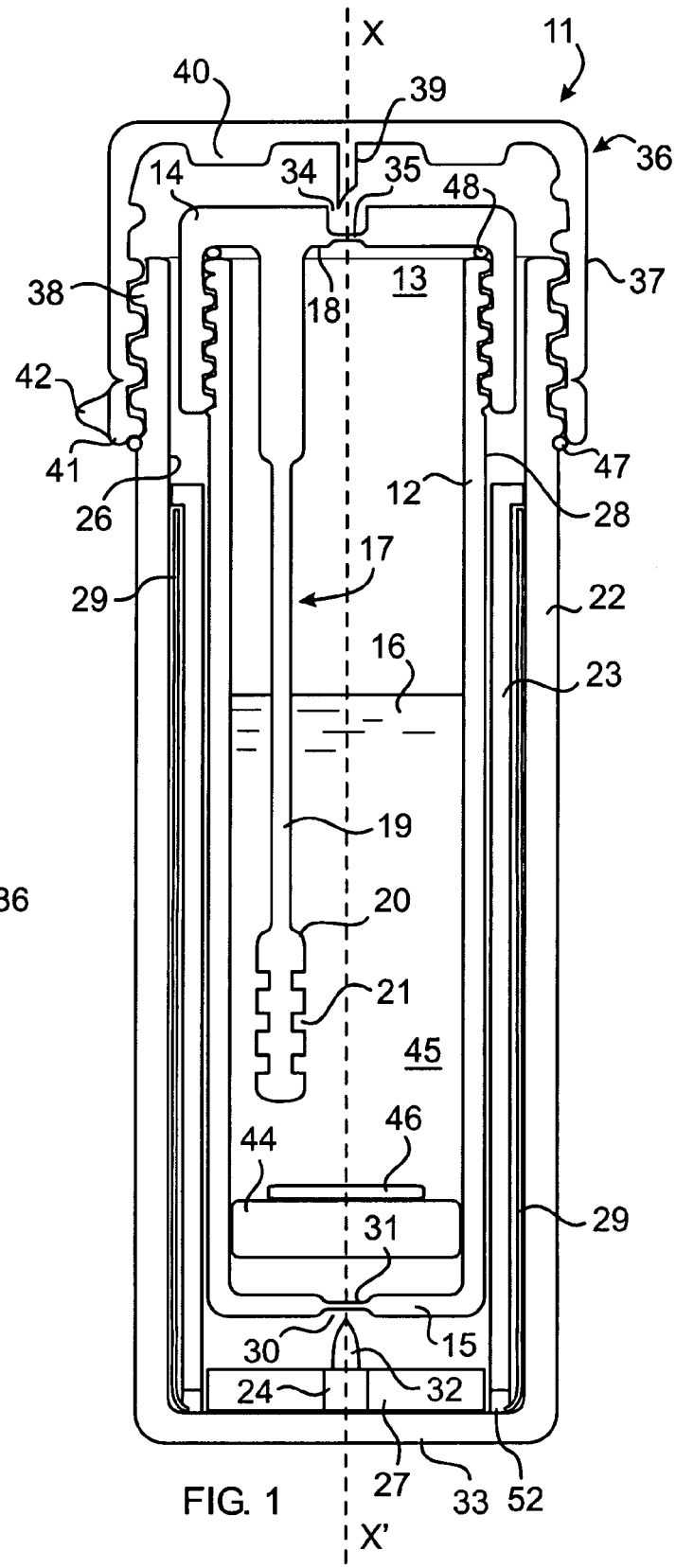
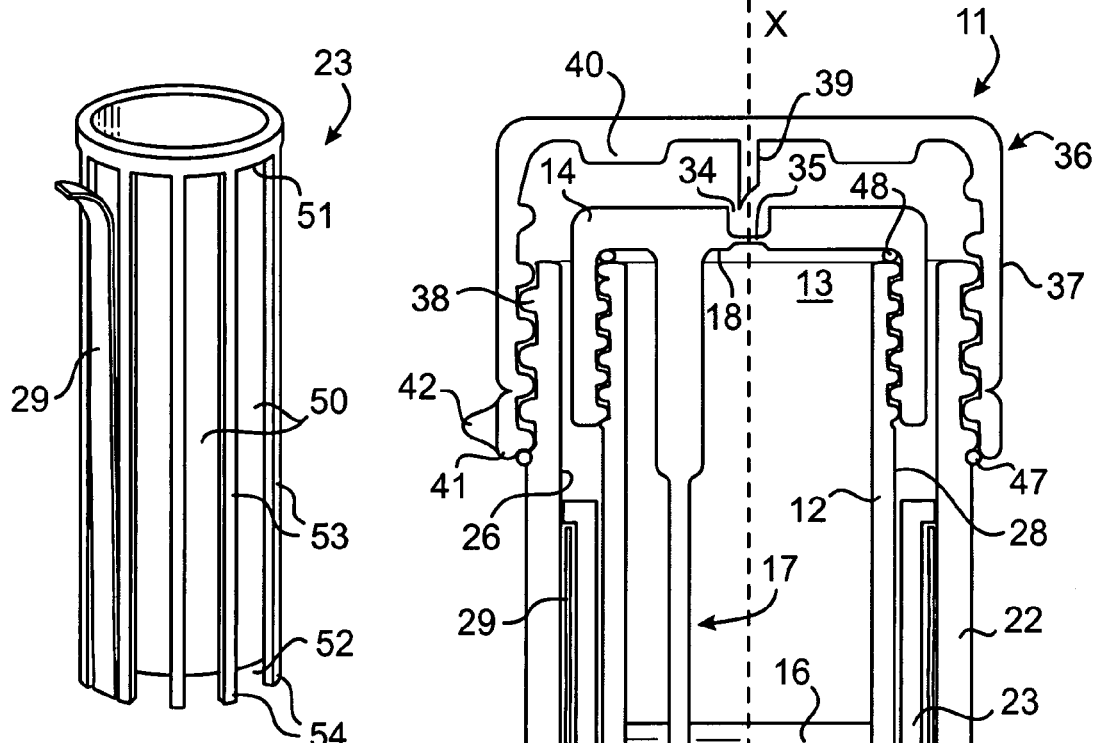
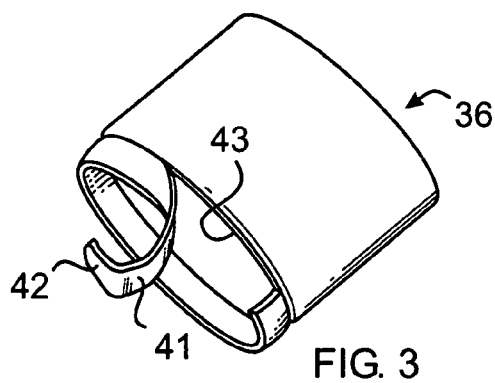
FIG. 2
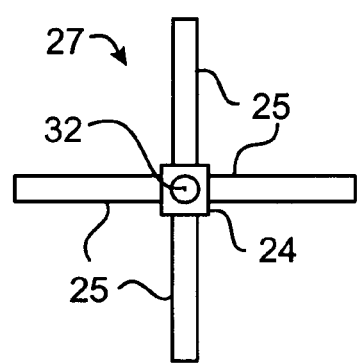
FIG. 3
FIG. 4
FIG. 1

ALL-IN-ONE BIOLOGICAL SPECIMEN COLLECTING, TRANSPORTING AND ANALYZING DEVICE

FIELD OF THE INVENTION

The present invention relates to immunoassay test devices and more specifically to devices for collecting, transporting and testing biological specimens by analysis using chromatographic immunoassay techniques.

BACKGROUND

Biological specimen testing, especially the testing of fecal samples is commonly used for detecting, diagnosing and monitoring a variety of diseases. Saliva swabs are often used to test for abused drugs. In most cases, a first instrument is used to collect a sample which is then packaged into a special enclosure for handling or shipping. In the laboratory, the specimen is usually diluted into a solution which is exposed to a mobilized binding member, conjugated to visually detectable label such as colloidal gold, that can bind to an analyte in the specimen which is specific to the condition being tested. Bound analytes are then analyzed by accumulation within a chromatographic immunoassay strip or the like having a region of immobilized binding members which signal the test result.

These various manipulations requires the handling of diverse containers and testing instruments. In order to simplify the procedure and reduce the risk of contamination, attempts have been made in the past to combine these containers and instruments. In a patent application disclosed in Publication No. U.S. 2006/0188939 Gao, a specimen collector and dissolving solution enclosure are packaged in a single housing for shipping. In the laboratory, that housing is coupled to a second enclosure containing one or more chromatographic testing strips. Upon coupling of the two enclosures, the analyte-containing solution is forced into the second one where it comes in contact with the testing strip.

The present invention results from an attempt to further simplify both the instrumentality and procedure for the sample collecting, shipping and analyzing processes.

SUMMARY

The invention allows for laboratory triggering and performance of the analyzing process by simply manipulating the cap of a shipping vessel containing the specimen collector and container without having to open the vessel or contact its contents.

In accordances with the purposes of the instant invention, a self-contained device for collecting, transporting and analyzing a biological specimen comprises an outer tubular enclosure having a top opening, a lateral wall and a closed bottom. A manipulable cap releasably seals the top opening. An inner second tubular enclosure is housed inside the outer enclosure. A sample collector has a portion releasably sealing the inner enclosure. The device has a means for causing a solution contained in the inner enclosure to partially flow into the outer enclosure upon manipulation of the cap in the absence of any contacting or manipulating of the inner enclosure and collector.

The inner enclosure has a first aperture sealed by a portion of the collector, a second aperture and a removable barrier closing the second aperture wherein the outer enclosure comprises an inner projection shaped, sized and positioned to contact and eliminate the removable barrier upon manipulation of the cap.

The sealing portion of the collector has a hole and comprises a frangible barrier closing the hole, and the cap comprise means for breaking the frangible barrier upon said manipulation.

Said means for breaking comprise a pin projecting from an under surface section of the cap.

The device further comprises a signaling element inserted between an outer surface section of the inner enclosure and an inner surface section of the lateral wall of the outer enclosure.

The signaling element comprises an immunoassay strip.

The device further comprises means for keeping parts of said inner enclosure apart from inner surface portions of the outer enclosure.

The specimen collector and the inner enclosure are coaxially held within the outer enclosure.

The cap comprises means for securing said cap on the second enclosure in a first position wherein the projection remains away from the removable barrier and the pin remains away from the frangible barrier, and means for securing the cap on the second enclosure in a second position wherein the removable barrier is disabled by the projection an the frangible barrier is broken by the pin.

The device further comprises a mobilized binding member specific an analyte in question inside the inner enclosure.

In a preferred embodiment of the invention, a specimen collection and examination device comprises a first vessel having an open upper end and a closed bottom end; a stopper shaped and dimensioned to seal said upper end. A specimen collector projects from an under portion of the stopper down to a lower region of the first vessel when the stopper is secured about said open end. The bottom end has an aperture and a first removable barrier sealing said aperture. A second vessel is shaped and sized to loosely, but completely, nest the first vessel and stopper. The second vessel has an open top and a closed bottom, a screwable cap shaped and dimensioned to seal the open top. A pintle extends upwardly from an inner area of the said closed bottom, At least one signaling element is held in the second vessel; and the device includes means for placing the first vessel into the second vessel whereby the pintle disables the barrier.

In the device, the stopper has a hole therethrough and a frangible barrier sealing the hole. A pin projects from an under section of the cap; and there are means for allowing the pin to break the frangible barrier when the cap is placed about the open top of the second vessel.

The device further comprises means for spacing the bottom end of the first vessel slightly apart from the closed bottom of the second vessel.

The means for spacing apart comprise a standoff projecting upwardly from said closed bottom.

The removable barrier comprises a frangible web.

The device further comprises at least one spacer positioned, shaped and dimensioned to keep an outer lateral section of the first vessel apart from an inner lateral section of the second vessel.

Said means for placing comprises means for securing the cap on the second vessel in a first position wherein the pintle remains away from the removable barrier and the pin remains away from the frangible barrier, and means for securing the cap on the second vessel in a second position wherein the removable barrier is disabled by the pintle and the frangible barrier is broken by the pin.

In the device, the specimen collector comprises a shaft and a head having a plurality of indentations.

The device further comprises means for aligning the pintle with the aperture and the pin with the hole.

The device further comprises at least one immunoassay testing strip mounted on the spacer.

BRIEF DESCRIPTION OF THE DRAWING

FIG. 1 is a cross-sectional view of a device according to the invention;

FIG. 2 is a perspective view of the strip holding spacer insert;

FIG. 3 is a perspective view of the outer vessel cap; and

FIG. 4 is a top plan view of the standoff.

DESCRIPTION OF THE PREFERRED EMBODIMENT

Referring now to the drawing, there is shown in FIG. 1, a self-contained device 11 for collecting, transporting and analyzing a biological specimen. In this embodiment, the device is specifically designed for use in connection with fecal specimens but could be readily adapted to collect saliva, other bodily fluids or various other materials such as food for contamination testing, or dust for the presence of illegal substances, for example.

The device comprises a first inner tubular vessel or enclosure 12 having an open upper end 13 sealed by a stopper 14 and a bottom end 15. The vessel contains a liquid solution 16, a specimen collector 17 projects downwardly from and under portion 18 of the stopper and has a shaft 19 which terminates at its tip into a head 20 having a plurality of indentations 21. A fecal sample can be collected by plunging the head 20 into fecal matter of which small volumes will be retained by the indentations 21. The first vessel 12 is inserted and completely and coaxially housed in a second tubular and preferably transparent vessel or enclosure 22. The coaxial alignment of the two vessels is assured by a spacer insert 23 more specifically illustrated in FIG. 2.

The spacer insert 23 is shaped and dimensioned to extend up to the inner walls 26 of the second, outer vessel 22 and form a number of pockets 50 each of which is shaped and dimensioned hold a chromatographic immunoassay strip 29 in an upright orientation against the inner wall 26 of the outer vessel 22 for convenient viewing during testing. Each pocket terminates at a closed upper end 51 to help restrict axial movement of the strip, and a lower end gap 52 for allowing fluid from the outer vessel to contact the bottom portion of a strip. The structure of the spacer can be conveniently molded from a unitary piece of plastic material so that adjacent pockets 50 are separated by vertical separator columns 53 which can have lower end prominences 54 to create the gaps 52. The spacer 23 is shaped and dimensioned to keep the outer wall surfaces 28 of the inner vessel 12 apart from the inner wall surface 26 of the outer vessel.

As shown in FIGS. 1 and 4, a standoff insert 27 is shaped and dimensioned to rest upon the inner bottom surface of the outer vessel 22 and below the bottom end 15 of the inner vessel 12. The standoff comprises a hub 24 from which radiates four arms 25 in a quadrangular pattern. An aperture 30 in the closed bottom of the first vessel is sealed by a removable barrier 31. That barrier may be constituted by a frangible web of glass or plastic of the same material as the inner vessel 12. A pintle 32 projects from the hub 24 upwardly from the closed bottom 33 of the outer vessel is aligned to penetrate the aperture 30 and to eliminate by breaking it, the barrier 31 when the inner vessel 12 is forcibly pushed all the way down the outer vessel 22. When this occurs, the solution 16 in the inner vessel partially flows into the outer vessel, through the gaps, and contacts the test strips 29. Alternately the spacer 23 and the standoff 27 can be formed from a unitary piece of material. Care must be taken however to ensure fluid communication between the pintle and the strip or strips.

In order to equilibrate the pressure within the two vessels and facilitate the flow of the solution from one vessel to the other, the stopper 14 of the inner vessel has a hole 34 sealed by a frangible barrier 35 of the same type as the bottom barrier 31.

The upper opening of the second vessel 22 is sealed by a cap 36 having an internally threaded peripheral flange 37 that screws over the threaded brim 38 of the outer vessel 22. A pin 39 projects downwardly from an under surface section of the cap 36 toward the hole 34 and frangible barrier 35.

When the cap 36 is only partially screwed upon the outer vessel, the pintle 32 remains away from the frangible barrier 31 at the bottom of the inner vessel, and the pin 39 remains away from the frangible barrier 35 in the stopper of the inner vessel. When the cap 36 is fully screwed upon the outer vessel opening, the pintle 32 and the pin 39 break their respective barriers with which they are aligned.

The alignment of the projection or pintle 32 with the aperture 30, and of the pin 39 with the hole 34 results from the fact these various elements are precisely and centrally located on the vertical axis X-X' of the device. The specimen collector 17 can be conveniently located at a position offset from the central vertical axis, or otherwise shaped so that it does not block the hole 34.

The downward pressure is applied upon the stopper 14 by a protrusion 40 formed in the under surface of the cap 36. The cap is prevented from being screwed to its farthest position by a removable base ring 41 which is formed integrally with the cap. A pull-tab 42 allows for convenient peeling off of the ring 41 from the lower edge 43 of the flange 37. A filter 44 is preferably installed in the bottom region 45 of the inner vessel. A dried deposit 46 of a mobilizable binding member specific to an analyte in question may be placed above the filter. Alternately, the mobilizable binding member can be predissolved in the solution 16.

O-rings 47 and 48 are preferably mounted on the stopper and the cap in order to provide a hermetic closure. Alternately, the tolerances and resiliency of the materials of the components can be selected to provide an adequate seal.

Once a specimen has been collected with the stopper and collector combination, it is dipped into the solution 16 by screwing the stopper 14 over the inner vessel 12. The inner vessel is then typically shipped to a laboratory for analysis where it is inserted into the outer vessel kept at the lab. Once the inner vessel is inserted into the outer vessel 22, the cap 36 is placed over the top opening of the outer vessel and screwed as far as the ring 41 will allow. The device can then be briefly stored until the analysis is initiated. In this way, a person more protected from contamination, such as one wearing gloves can preload the inner vessel into the outer vessel, and a second, less protected worker can initiate the test. The analysis of the specimen can be performed without contacting or manipulating the inner vessel or the collector. The analysis is initiated by peeling off the ring 41 and screwing the cap 36 as far as it will go. Upon puncture of the barriers 31 and 35, the solution 16 containing particles of the specimen processed by exposure to mobilized binding members is filtered and partially flows into the second vessel 22 through the gaps formed by the spacer 23, and contact the immunoassay strips 29.

While the preferred embodiment of the invention has been described, modifications can be made and other embodiments may be devised without departing from the spirit of the invention and the scope of the appended claims.

What is claimed is:

1. A specimen collection and examination device which comprises:
   a first vessel having an open upper end and a closed bottom end;
   a stopper shaped and dimensioned to seal said open upper end;
   a specimen collector projecting from an under portion of said stopper down to a lower region of said first vessel when said stopper is secured about said open upper end;
   said closed bottom end having an aperture and a first removable barrier sealing said aperture;
   a second vessel separate and distinct from said first vessel and being shaped and sized to completely house said first vessel;
   said first vessel having a first position and a second position within said second vessel;
   a pintle extending from an inner area of said second vessel toward said first removable barrier when said first vessel is in said first position;
   at least one signaling element held in said second vessel; and
   said pintle being located and dimensioned to break said first removable barrier when said first vessel is placed in said second position.

2. The device of claim 1, wherein said stopper has a hole therethrough and a frangible barrier sealing said hole, and wherein said device further comprises:
   said second vessel having an open top;
   a cap shaped and dimensioned to seal said open top;
   a pin projecting from an under section of said cap; and
   said pin being aligned to break said frangible barrier when said cap is placed about the open top of said second vessel.

3. The device of claim 2, which further comprises:
   said hole and said pin being located substantially along a central axis of said device; and,
   said specimen collector being located at a position offset from said central axis.

4. The device of claim 2, which further comprises an insert spacing said first vessel slightly apart from said second vessel.

5. The device of claim 4, wherein said second vessel has a closed bottom, and wherein said insert comprises a standoff projecting upwardly from said closed bottom.

6. The device of claim 4, wherein said insert is shaped and dimensioned to align said pintle with said aperture and said pin with said hole.

7. The device of claim 1, wherein said first removable barrier comprises a frangible web.

8. The device of claim 4, wherein said insert further comprises at least one spacer positioned, shaped and dimensioned to keep an outer lateral section of said first vessel apart from an inner lateral section of said second vessel.

9. The device of claim 2, which further comprises:
   a removable member keeping said cap in a first cap position wherein said pintle remains away from said first removable barrier and said pin remains away from said frangible barrier; and
   wherein removing said member allows said cap to be placed in a second cap position allowing said frangible barrier to be broken by said pin.

10. The device of claim 1, wherein said specimen collector comprises:
    a shaft; and
    a head having at least one indentation.

* * * * *